United States Patent [19]

Frieben et al.

[11] Patent Number: 4,621,145

[45] Date of Patent: Nov. 4, 1986

[54] PROCESS FOR PREPARING 5-VINYL-2-PYRROLIDINONE AND INTERMEDIATES THEREFOR

[75] Inventors: Wolfgang Frieben, Willstatt-Sand; Fritz Gerhart, Kehl-Leutesheim, both of Fed. Rep. of Germany

[73] Assignee: Merrell Dow Pharmaceuticals Inc., Cincinnati, Ohio

[21] Appl. No.: 556,204

[22] Filed: Nov. 29, 1983

[30] Foreign Application Priority Data

Dec. 30, 1982 [GB] United Kingdom ............... 8236998

[51] Int. Cl.$^4$ ........................................... C07D 207/36
[52] U.S. Cl. ..................................................... 548/543
[58] Field of Search ........................................ 548/543

[56] References Cited

PUBLICATIONS

Finar, Org. Chem., vol. 1, pp. 301 & 302, (1959).
Cope et al., JACS, 79, 4720–29, (1957).

Primary Examiner—Glennon H. Hollrah
Assistant Examiner—D. B. Springer
Attorney, Agent, or Firm—Stephen L. Nesbitt; William J. Stein

[57] ABSTRACT

4-Amino-5-hexenoic acid is prepared by:
  (a) reacting 5-oxo-2-pyrrolidine-acetonitrile with hydrogen and dimethylamine in the presence of a palladium catalyst to form N,N-dimethyl-2-[5′-oxo-2′-pyrrolidine]ethylamine;
  (b) oxidizing N,N-dimethyl-2-[5′-oxo-2′-pyrrolidine]ethylamine to produce the corresponding N-oxide derivative;
  (c) pyrolysis of the N-oxide derivative to form 5-vinyl-2-pyrrolidinone;
  (d) optionally, separating N,N-dimethyl-2-[5′-oxo-2′-pyrrolidine]ethylamine by-product from the 5-vinyl-2-pyrrolidinone product; and
  (e) hydrolyzing 5-vinyl-2-pyrrolidinone to form 4-amino-5-hexenoic acid.

4 Claims, No Drawings

PROCESS FOR PREPARING 5-VINYL-2-PYRROLIDINONE AND INTERMEDIATES THEREFOR

The present invention is directed to a novel process for preparing 4-amino-5-hexenoic acid and to novel intermediates employed in the process.

4-Amino-5-hexenoic acid (also known as 4-vinyl-4-aminobutyric acid, γ-vinyl-γ-aminobutyric acid, or "vinyl-GABA") is described in U.S. Pat. No. 3,960,927. 4-Amino-5-hexenoic acid is an irreversible inhibitor of γ-aminobutyric acid transaminase (GABA-T) and is, therefore, capable of increasing the level of γ-aminobutyric acid (GABA) in the CNS. The compound is useful for treating disorders associated with depletion of GABA levels in the CNS, for example, tardive dyskinesia, schizophrenia, and seizure disorders such as epilepsy. The biochemical and pharmacological effects of 4-amino-5-hexenoic acid are described in Lippert et al., Eur. J. Biochem., 74, 441 (1977), Metcalf, Biochemical Pharmacology, 28, 1705 (1979), Lippert et al., Brain Research Bulletin, 5, 375 (1980), and Palfreyman et al., Biochemical Pharmacology, 30, 817 (1981).

U.S. Pat. Nos. 4,178,463, 4,235,778, and 4,254,204 disclose the preparation of 4-amino-5-hexenoic acid by reacting a suitable derivative of 2-vinylcyclopropane-1,1-dicarboxylic acid with ammonia to form a 3-[carboxy-, carboxamido-, or tert-butoxycarbonyl]-5-vinyl-2-pyrrolidinone and treating the 3-[carboxy-, carboxamido-, or tert-butoxycarbonyl]-5-vinyl-2-pyrrolidinone with a strong acid. The patents also describe the decarboxylation of a 3-[carboxy-, carboxamido-, or tert-butoxycarbonyl]-5-vinyl-2-pyrrolidinone to afford 5-vinyl-2-pyrrolidinone which can then be converted via bromination and dehydrobromination to 5-ethynyl-2-pyrrolidinone which can be hydrolyzed to 4-aminohex-5-ynoic acid. 4-Aminohex-5ynoic acid is described in U.S. Pat. No. 3,959,356.

In a first process aspect, the present invention provides a process for preparing 5-vinyl-2-pyrrolidinone which comprises:

(a) reacting 5-oxo-2-pyrrolidine-acetonitrile with hydrogen and dimethylamine in the presence of a palladium catalyst to form N,N-dimethyl-2-[5'-oxo-2'-pyrrolidine]ethylamine;

(b) oxidizing N,N-dimethyl-2-[5'-oxo-2'-pyrrolidine]ethylamine with an oxidizing agent to produce the corresponding N-oxide derivative;

(c) pyrolysis of the N-oxide derivative to form 5-vinyl-2-pyrrolidinone; and, optionally, (d) separating N,N-dimethyl-2-[5'-oxo-2'-pyrrolidine[ethylamine by-product from 5-vinyl-2-pyrrolidinone product.

In a second process aspect, the invention provides a process for preparing 4-amino-5-hexenoic acid which comprises preparing 5-vinyl-2-pyrrolidinone according to Steps (a), (b), (c), and (d) as described hereinabove and then hydrolyzing the 5-vinyl-2-pyrrolidinone product.

In a third process aspect, the invention provides a process for preparing 5-vinyl-2-pyrrolidinone which comprises the pyrolysis of the N-oxide of N,N-dimethyl-2-[5'-oxo-2'-pyrrolidine]ethylamine and, optionally, separating N,N-dimethyl-2-[5'-oxo-2'-pyrrolidine]ethylamine by-product from the 5-vinyl-2-pyrrolidinone product.

In a fourth process aspect, the invention provides a process for preparing N,N-dimethyl-2-(5'oxo-2'-pyrrolidinone)ethylamine, or the N-oxide thereof, which comprises reacting 5-oxo-2-pyrrolidineacetonitrile with hydrogen and dimethylamine in the presence of a palladium catalyst, and, when the N-oxide is required, oxidizing the N,N-dimethyl-2-[5'-oxo-2'-pyrolidinone]ethylamine product of acid reaction.

The preparation of N,N-dimethyl-2-[5'-oxo-2'-pyrrolidinone]ethylamine, the N-oxide thereof, 5-vinyl-2-pyrrolidinone, and 4-amino-5-hexenoic acid from 5-oxo-2-pyrrolidineacetonitrile is depicted schematically below in FIGURE 1:

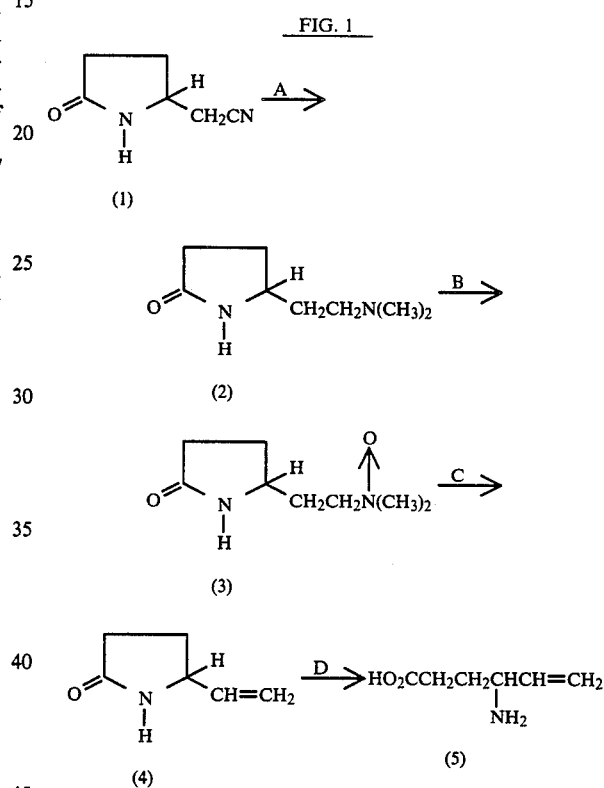

In Step A, 5-oxo-2-pyrrolidinoneacetonitrile (1) is reacted with hydrogen gas and dimethylamine in the presence of a palladium catalyst, such as palladium-on-barium sulfate or palladium-on-aluminium oxide (Al₂O₃) to produce N,N-dimethyl-2-[5'-oxo-2'-pyrrolidine]ethylamine (3). This reaction is analogous to that described by Kindler et al., Arch. Pharm., 283, 184 (1950). The reaction can be carried out in an inert solvent, preferably a ($C_1$–$C_6$)alkanol or water, at a temperature from about 20° to 100° C. Ambient temperature is preferred. The hydrogen gas pressure can range from about one atmosphere to about 20 atmospheres. Two atmospheres are preferred. The reaction time will vary depending upon the temperature and pressure. The product of the reaction is recovered from the reaction mixture by conventional procedures. A preferred procedure involves filtering the reaction mixture to remove the catalyst, evaporating the solvent from the filtrate to give a residue, and distillating the residue under vacuum. This procedure will remove dimeric and trimeric by-products which interfere with the next step of the process.

In Step B, N,N-dimethyl-2-[5'-oxo-2'-pyrrolidine]ethylamine (2) is oxidized in manner known per se to give the corresponding N-oxide derivative (3). The oxidizing agent employed in Step B can be any reagent known in the art to be useful for oxidizing a tertiary amine to the corresponding N-oxide derivative. Suitable reagents, conditions, and solvents for the oxidation reaction will be apparent to those skilled in the art. A preferred reagent is hydrogen peroxide in water, for example, 30% hydrogen peroxide-water, or in a ($C_1$-$C_6$)-alkanol, for example, methanol or ethanol, or mixtures thereof. Organic peracids, such as peracetic acid, performic acid, perbenzoic acid, m-chloroperbenzoic acid, or perphthalic acid can also be employed. The following are examples of solvents that can be used with organic peracids: tetrahydrofuran and chloroform (perbenzoic and m-chloroperbenzoic acids), benzene (perbenzoic acid), diethyl ether (peracetic acid). Peracetic acid can also be used without an additional solvent. Other oxidizing agents are inorganic peracids, for example, persulfuric acid, and ozone. Persulfuric acid can be used without an additional solvent. Ozone can be used in chloroform or dilute sulfuric acid. For the peracids, the oxidation reaction can be carried out at a temperature ranging from about $-5°$ to about $50°$ C. Ambient temperature is preferred. For ozone, the reaction can be carried out at $-78°$ C. The N-oxide derivative is recovered from the oxidation reaction mixture but need not be purified. The recovery of the N-oxide derivative can be accomplished using conventional techniques. For example, when 30% hydrogen peroxide-water is employed as the oxidizing agent, the N-oxide conveniently can be recovered by treating the reaction mixture with platinium black or catalase (or other suitable peroxide-destroying reagent) to destroy excess hydrogen peroxide, filtering the mixture, extracting the filtrate with chloroform, separating the aqueous phase, and evaporating solvent from the aqueous phase to give the N-oxide derivative as a residue.

In Step C, the N-oxide derivative (3) formed in Step B undergoes the Cope elimination to afford 5-vinyl-2-pyrrolidinone (4). The elimination is accomplished in manner known per se by pyrolysis of the N-oxide derivative. Usually the pyrolysis will be carried out at a temperature of at least $140°$ C. under reduced pressure. Suitably the temperature of the pyrolysis reaction can range from about $140°$ to about $185°$ C., preferably $150°$ C. Conveniently the pyrolysis can be carried out dry under reduced pressure so that the product, 5-vinyl-2-pyrrolidinone, will continuously distil from the reaction mixture. The elimination reaction may be accompanied by a deoxygenation reaction whereby N,N-dimethyl-2-[5'-oxo-2'-pyrrolidine]ethylamine is produced as a by-product. When the pyrolysis is carried out under reduced pressure, the by-product can distil from the reaction mixture along with 5-vinyl-2-pyrrolidinone. If it is desired to separate the by-product, an aqueous solution of the distillate can be treated with a sufficient amount of an acidic ion exchange resin, such as Amberlite IR 120, $H^+$ form, until the solution shows a neutral pH, whereby the basic by-product becomes bound to the acidic resin and is effectively removed from solution containing the desired product. The resin containing the by-product and any unreacted resin can then be separated from the solution by filtration. The neutral aqueous filtrate can be used directly in Step D or it can be further treated in manner known per se in order to recover 5-vinyl-2-pyrrolidinone. The recovery of 5-vinyl-2-pyrrolidinone can be accomplished by evaporating solvent from the neutral filtrate to give a residue, and distilling the residue under vacuum. 5-Vinyl-2-pyrrolidinone thus obtained can be re-dissolved in water, and the resulting solution can be subsequently used in Step D.

If desired, the resin which is removed by filtration can be treated in known manner so as to regenerate N,N-dimethyl-2-[5'-oxo-2'-pyrrolidine]ethylamine (2), which can then be recycled in step B.

Other methods known in the art, such as chromatography, can be used, if desired, to separate the by-product.

In Step D, 5-vinyl-2-pyrrolidinone (4) is hydrolyzed in known manner per se to give the desired final product, 4-amino-5-hexenoic acid (5). Conditions for opening the lactam ring by acid hydrolysis are well known in the art. For example, a strong acid, such as hydrochloric acid, or trifluoroacetic acid, can be added to an aqueous solution of 5-vinyl-2-pyrrolidinone (for example, as obtained from Step C) and the resulting solution can be heated, preferably above $60°$ C. A most preferred hydrolysis procedure is to heat 5-vinyl-2-pyrrolidinone in 5% aqueous hydrochloric acid at a temperature of $95°$ to $100°$ C.

In the acid hydrolysis performed in Step D, 4-amino-5-hexenoic acid forms an acid addition salt with the strong acid present in the reaction medium. The acid addition salt can be isolated as a residue after evaporating solvent from the reaction medium. The residue can be purified by conventional means, such as recrystallization. If desired, 4-amino-5-hexenoic acid in the form of the free base or zwitterion can be obtained by contacting the acid addition salt with a strong base. The free base or zwitterion thus formed can be isolated by conventional means. For example, when the hydrolysis of 4-amino-5-hexenoic acid is carried out using 5% hydrochloric acid, the residue obtained after evaporation of solvent from the reaction medium is dissolved in ethanol/isopropanol, triethylamine is added to the resulting solution to pH 7-8, and the product is separated by precipitation. The precipitate can be purified by dissolving it in water, heating the resulting solution with charcoal ($90°$ C.), filtering the mixture, and adding ethanol and isopropanol to the filtrate. Pure 4-amino-5-hexenoic acid will crystallize upon standing at $5°$ C.

FIGURE 2, set forth below, depicts an appropriate method for preparing 5-oxo-2-pyrrolidine-acetonitrile (1), which is the starting material employed in the process of this invention [See FIGURE 1, Step A, Compound (1)].

FIG. 2

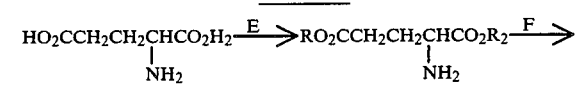

(5)                    (6)

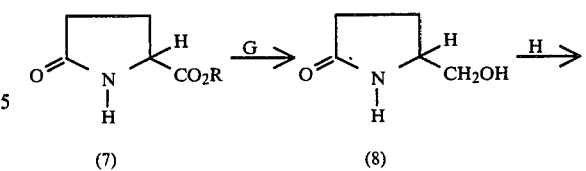

(7)                    (8)

-continued
FIG. 2

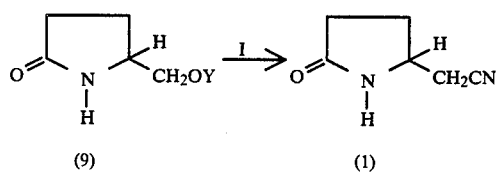

In FIGURE 2, R is $(C_1-C_6)$alkyl group and —OY is p-toluenesulfonyloxy (tosyloxy) or methanesulfonyloxy (mesyloxy).

In Step E, L- or DL-glutamic acid (5) is esterified in known manner to give the diester (6). Any conventional esterification method can be used. For example, L- or DL-glutamic acid (5) can be treated with thionyl chloride and ethanol to give diethyl glutamate.

In Step F, the diester (6) undergoes a cyclization reaction to give a pyroglutamic acid ester (7). The cyclization is accomplished in known manner by pyrolysis. The temperature of the pyrolysis can range from about 150° C. to 200° C. It is preferred to carry out the pyrolysis under reduced pressure so that the pyroglutamic acid ester (7) continuously distills from the reaction mixture.

In Step G, the pyroglutamic acid ester (7) is reduced to give 5-hydroxymethyl-2-pyrrolidinone (8). The reduction conditions employed must be capable of reducing the ester carbonyl without reducing the lactam carbonyl. Suitable reducing agents are lithium borohydride in tetrahydrofuran, sodium borohydride in water or ethanol, or DIBAL-H. Sodium borohydride in water or ethanol is preferred.

In Step H, 5-hydroxymethyl-2-pyrrolidinone (8) is converted in known manner to the corresponding tosyloxy or mesyloxy derivative (9). One method is to treat 5-hydroxymethyl-2-pyrrolidinone with tosylchloride or mesylchloride in dry pyridine. Another method for carrying out the transformation involves reacting 5-hydroxymethyl-2-pyrrolidinone with tosylchloride or mesylchloride and sodium hydroxide in methylene chloride/water in the presence of a phase transfer catalyst, such as tetra-n-butylammonium hydrogen sulfate.

In Step I, the tosyloxy or mesyloxy derivative (9) is converted in known manner to 5-oxo-2-pyrrolidine-acetonitrile (1). The conversion can be accomplished by treating the tosyloxy or mesyloxy derivative (9) with sodium cyanide and sodium iodide in dry dimethylformamide. 5-Oxo-2-pyrrolidine-acetonitrile must be obtained free of sodium cyanide to avoid interferences during Step A of the subsequent reaction sequence.

Since 4-amino-5-hexenoic acid possesses a chiral center, optical isomers are possible, and 4-amino-5-hexenoic acid and the intermediates thereto shown in FIGURE 1 can exist in the form of a pure enantiomer or a mixture of enantiomers, such as the racemate. As will be recognized by those skilled in the art, the processes of this invention can be employed to make each substantially pure individual enantiomer or the racemate of 4-amino-5-hexenoic acid, or of the intermediates thereto, depending upon the optical configuration of 5-oxo-2-pyrrolidine-acetonitrile, which is used as the starting material of the over-all process (See Step A, FIGURE 1). The starting materials and the intermediates and products produced therefrom by the process depicted in FIGURE 1 are shown below:

| Starting Material (Compound 1) | Intermediates (Compounds 2, 3, and 4) | Product (Compound 5) |
|---|---|---|
| (S)—5-oxo-2-pyrrolidine-acetonitrile | (S)—N,N—dimethyl-2-[5'-oxo-2'-pyrrolidine]ethylamine; the N—oxide thereof; and (S)—5-vinyl-2-pyrrolidinone | (S)—4-amino-5-hexenoic acid |
| (R,S)—5-oxo-2-pyrrolidine-acetonitrile | (R,S)—N,N—dimethyl-2-[5'-oxo-2'-pyrrolidine]ethylamine; the N—oxide thereof; and (S)—5-vinyl-2-pyrrolidinone | (R,S)—4-amino-5-hexenoic acid |
| (R)—5-oxo-2-pyrrolidine-acetonitrile | (R)—N,N—dimethyl-2-[5'-oxo-2'-pyrrolidine]ethylamine; the N—oxide thereof; and (S)—5-vinyl-2-pyrrolidinone | (R)—4-amino-5-hexenoic acid |

It has been found that the biologically active enantiomer of (4)-amino-5-hexenoic acid is the (+)-enantiomer, which is (S)-4-amino-5-hexenoic acid. Thus, the pure biologically active (S)-enantiomer or the racemate (i.e. the R,S-form) of 4-amino-5-hexenoic acid can be employed in vivo to inhibit GABA-T enzyme. The biologically inactive (R)-enantiomer of 4-amino-5-hexenoic acid can be converted, however, in manner known per se to the (R)-enantiomer of 4-aminohex-5-ynoic acid. The method for preparing (R)-4-aminohex-5-ynoic acid from (R)-4-amino-5-hexenoic acid is illustrated in Examples 10 to 13. The conversion of 5-vinyl-2-pyrrolidinone to 4-aminohex-5-ynoic acid via 5-ethynyl-2-pyrrolidinone is also described in U.S. Pat. No. 4,178,463.

The biochemical and pharmacological effects of 4-aminohex-5-ynoic acid are described in Jung et al., Biochem. and Biophys. Res. Comm., 67, 301 (1975); Jung et al., J. Neurochemistry, 28, 717 (1977); Jung et al., Biochemistry, 17, 2628 (1978); Bouclier et al., Eur. J. Biochem., 98, 363 (1979); Biochem. Pharmacology, 28, 1705 (1979); and Lippert et al., Brain Research Bull., 5, 375 (1980). It has been reported by Lippert et al., supra and Bouclier et al., supra, that the (+)-enantiomer of 4-aminohex-5-ynoic acid, which is (S)-4-aminohex-5-ynoic acid, is the only enantiomer of 4-aminohex-5-ynoic acid which will irreversibly inhibit GABA-T. More recent experiments have demonstrated, however, that the (R)-enantiomer is an irreversible inhibitor of GABA-T both in vivo and in vitro. For example, (R)-4-aminohex-5-ynoic acid gave the follow effects on GABA-T activity and GABA concentrations in mice brain using the test method of Jung et al., J. Neurochemistry, supra:

| Dose (mg/kg) | % Inhibition of GABA-T[a] | GABA Concentration % Control[a] |
|---|---|---|
| control | 0 | 100 |
| 25 | 31 | 103 |
| 50 | 50 | 125 |
| 100 | 66 | 180 |
| 200 | 81 | 275 |

[a]4 hours after injection of the test compound, i.p.

In a chronic experiment, a group of five rats was given oral daily doses of 100 mg/kg of (R)-4-aminohex-5-ynoic acid. A separate group of animals was used as control. Twenty-four hours after the last dose, the animals were sacrificed and the cortex was dissected from the rest of the brain. GABA-T activity was measured in homogenates of brain minus the cortex and was found to be decreased by 81% in the animals treated with (R)-4-aminohex-5-ynoic acid as compared to controls. GABA concentration was measured in homogenates of the cortex and was found to be approximately doubled in the animals treated with (R)-4-aminohex-5-ynoic acid. During the first week of treatment, the animals lost body weight and lost hair on their backs. These effects appeared to disappear during the second week, however.

At dosages of 100 and 200 mg/kg, administered i.p., (R)-4-aminohex-5-ynoic acid was shown to protect mice against convulsions and death, induced by mercaptopropionic acid, administered at a dose of 53 mg/kg, i.p., 6 hours after injection of (R)-4-aminohex-5-ynoic acid. However, no protection against running fits was afforded.

At a single dose of 400 mg/kg, i.p., in mice, (R)-4-aminohex-5-ynoic acid produced sedation within 30 minutes, but 24 hours later the animals were dead.

(S)-5-Oxo-2-pyrrolidine-acetonitrile [Compound (1)] and its preparation from L-glutamic acid via (S)-5-tosyloxymethyl-2-pyrrolidinone by the reaction sequence shown in FIGURE 2 (Steps E, F, G, H, and I) are described by Hardegger and Ott, *Helv. Chim. Acta*, 38, 318 (1955). The reduction of ethyl-(S)-pyroglutamate with sodium borohydride in ethanol is described by Saijo et al., *Chem. Pharm. Bull.*, 28, 1449 (1980). The reduction of ethyl-(S)-pyroglutamate with lithium borohydride is described by Bruckner et al., *Acta Chim. Hung.*, 21, 105, 116 (1959). The preparation of ethyl-(S)-pyroglutamate from diethyl L-glutamate is described by Fischer and Boehner, *Chem. Ber.*, 44, 1333 (1911) and Abderhalden and Wield, *Hoppe-Seiler's Z.f. Physiol, Chem.*, 74, 459 (1911).

In its composition-of-matter aspects, the present invention comprehends N,N-dimethyl-2-[5'-oxo-2'-pyrrolidine]ethylamine or the N-oxide thereof, or an acid addition salt thereof.

The following Examples will illustrate processes for carrying out the invention. As employed in the Examples, "THF" means tetrahydrofuran and "DMF" means dimethylformamide. Drying of organic extracts was accomplished using anhydrous sodium sulfate.

EXAMPLE 1

Ethyl L-pyroglutamate

Thionyl chloride (217 ml) is slowly added to a stirred suspension of L-glutamic acid (417 g) in dry ethanol (1 L), and the mixture is refluxed for 5 hours. Ethanol is removed under vaccum to give a residue, which is dissolved in water (500 ml). The water solution is made alkaline with saturated sodium carbonate solution and extracted with chloroform (4×200 ml). The chloroform extract is dried (Na2SO4) and evaporated to give crude product (178 g). This material is heated (160° C.) under vaccum (10 mm Hg) for 3 hours. Subsequent distillation gives pure ethyl L-pyroglutamate (126.6 g; b.p. 126° C./0.07 mm Hg; [α]$_D$= −2.15°±0.01 (H2O, c=17.8).

EXAMPLE 2

(S)-5-Hydroxymethyl-2-pyrrolidinone

Under an atmosphere of nitrogen, ethyl L-pyroglutamate (31.4 g), obtained as in Example 1, dissolved in THF (100 ml), is added slowly to a stirred suspension of lithium borohydride (8 g) in dry THF (260 ml). During the addition, the temperature is kept below 40° C. The mixture is then stirred at room temperature for 48 hours. Water (50 ml) and THF (150 ml) is added, and the resulting mixture is stirred overnight. Filtration (methanol washing) and evaporation of solvent gives a residue which is digested with methanol (100 ml). The mixture is filtered (chloroform washing, 100 ml), evaporated and dissolved in chloroform again. Filtration and evaporation give the title compound as an oil: 24.2 g.

EXAMPLE 3

(S)-5-[Methanesulfonyloxy]-methyl-2-pyrrolidinone

Crude (S)-5-hydroxymethyl-2-pyrrolidinone (13 g), obtained as in Example 2, dissolved in dry pyridine (120 ml), and cooled with ice, is treated with mesylchloride (10 ml), keeping the temperature below 5° C. The mixture is allowed to warm to room temperature and is stirred for 1 more hour. Water (2 ml) is added, and the mixture is stirred for 10 more minutes. The solvent is removed under vacuum, and the residue obtained is digested with dichloromethane. The mixture is filtered (methylene chloride-washing) and solvent is removed by evaporation to give a residue. The residue is dissolved in water (100 ml) and the resulting solution is treated with a cation exchange resin (H⊕-form, 2 g) and an anion exchanger (OH⊖-form, 2 g). Filtration and evaporation give an oil which is dissolved in chloroform. After removal of insoluble material, drying and evaporation give crude title compound, 16.8 g. This material is recrystallized from cold methanol to yield 12.12 g.

EXAMPLE 4

(S)-5-Oxo-2-pyrrolidine-acetonitrile

A mixture of (S)-5-[methanesulfonyloxy]methyl-2-pyrrolidinone (19.3 g), obtained as in Example 3, sodium cyanide (7.3 g), sodium iodide (50 mg), and dry DMF (100 ml) is stirred and heated at 90° C. for 3 hours. Stirring is continued at room temperature overnight. Salts are then removed by filtration (dichloromethane washing). The residue obtained on evaporation is dissolved in dichloromethane (50 ml), insoluble material is filtered off, and the filtrate is evaporated again. Ethyl acetate (5 ml) is added. Crude title compound (11.4 g) crystallizes upon standing overnight (5° C.). Recrystallization from ethyl acetate/diethyl ether gives the pure title compound (9.2 g).

EXAMPLE 5

(S)-N,N-Dimethyl-2-[5'-oxo-2'-pyrrolidine]-ethylamine

To a solution of (S)-5-oxo-2-pyrrolidine-acetonitrile (9.42 g, 80 mmole), obtained as in Example 4, in ethanol (80 ml), a 33% solution of dimethylamine in ethanol (28 ml) is added, and the resulting mixture is hydrogenated overnight (30 p.s.i.) in the presence of palladium-on-barium sulfate (5%, 12 g). Distillation gives the title compound (8.63 g, (b.p. 105°–110° C./0.15 mm Hg.

EXAMPLE 6

(S)-5-Vinyl-2-pyrrolidinone (S)-N,N-Dimethyl-2-[5'-oxo-2'-pyrrolidine]ethylamine (3.69 g), obtained as in Example 5, dissolved in water (10 ml), is treated with 30% hydrogen peroxide (2.66 g). After 2 hours, more hydrogen peroxide (2.66 g) is added, and stirring is continued for 60 hours. A third portion of 30% hydrogen peroxide (2.65 g) is then added, and stirring is continued for another 24 hours to complete the oxidation (pH neutral). The excess of hydrogen peroxide is destroyed by stirring (12-24 hours) with a few mg of catalase; absence of hydrogen peroxide is tested for with "Merckoquant" peroxide test paper. The mixture is filtered and evaporated to give the crude N-oxide (presumably as a hydrate) as an oil (4.7 g). This oil is heated under vacuum (0.1 mm Hg). At 130° C., the material solidifies, and at 160° C. (bath temperature), the title compound distils (2.3 g). According to MS analysis, the crude product contains ≦40% of (S)-N,N-dimethyl-2-[5'-oxo-2'-pyrrolidine]ethylamine.

EXAMPLE 7

(S)-4-Amino-5-hexenoic acid

Crude (S)-5-vinyl-2-pyrrolidinone (1.97 g), obtained as in Example 6, is heated with 5% aqueous hydrochloric acid (50 ml) at 95° C. for 5 hours. After evaporation of solvent, the resulting residue is dissolved in a mixture of ethanol (5 ml) and isopropanol (12 ml). Upon addition of triethylamine until pH 7-8, the crude title compound precipitates (1.0 g). This material is dissolved in water (2 ml). Treatment with charcoal (90° C., 30 minutes), and addition of ethanol (10 ml) and isopropanol (2 ml) give pure title compound which crystallizes on standing at 5° C. overnight. Addition of more isopropanol gives a second crop; total: 450 mg; $[\alpha]_D = 12.4 \pm 0.6$ (H$_2$O, c=0.515), 6C (opt. active column+MS): optical purity at best 99% (no R-isomer detectable).

EXAMPLE 8

(S)-5-Vinyl-2-pyrrolidinone

The oxidation of (S)-N,N-dimethyl-2-[5'-oxo-2'-pyrrolidine]ethylamine is repeated according to the procedure of Example 6. Excess of hydrogen peroxide is destroyed with platinum black. The mixture is filtered and the filtrate is extracted with chloroform. The aqueous phase is evaporated to give a residue. This is dissolved in a few ml of ethanol. Evaporation of solvent gives the N-oxide (presumably as the hydrate) as a white solid. Recrystallization from ethanol gives 7.1 g of material (starting from 8.63 g of the amine starting material). On dry distillation, (S)-5-vinyl-2-pyrrolidinone distills at 150° C. (0.1 mm Hg) bath temperature. The temperature is raised finally to 185° C. According to NMR analysis, the slightly yellow coloured distillate (4.07 g) contains about 25 mole-% of (S)-N,N-dimethyl-2-[5'-oxo-2'-pyrrolidine]ethylamine. The distillate is dissolved in water (60 ml), and the resulting solution is treated with an ion exchange resin (Amberlite R 150, H+-form) until neutral (10 ml of wet resin). Filtration, evaporation, and distillation (b.p. 130° C./0.1 mm Hg) give (S)-5-vinyl-2-pyrrolidinone as a colourless liquid [2.486 g, hygroscopic, purity ≧98% (GC/MS)]. The resin is collected and treated with 6N HCl (2×50 ml) and washed with water (50 ml). Evaporation of solvent gives (S)-N,N-dimethyl-2-[5'-oxo-2'-pyrrolidine]ethylamine (as the hydrochloride) as a solid (1.47 g).

EXAMPLE 9

(S)-5-Tosyloxymethyl-2-pyrrolidinone

Ethyl (L)-pyroglutamate (15.7 g), dissolved in water (50 ml) is added slowly at 0° C. to a solution of sodium borohydride (2.2 g) in water (50 ml). The mixture is allowed to warm up over a one-hour period after which it is stirred at room temperature for 20 minutes. Acetone (5 ml) is added and the stirring is continued for 30 minutes. Solvent is evaporated to give a dry residue which is dissolved in water (100 ml). The solution is then concentrated to a volume of 40 ml. To the concentrated solution are added: caustic soda (5 g), tosyl chloride (18.10 g) in dichloromethane (100 ml), and tetra-n-butyl ammonium hydrogen sulfate (1.03 g). The resulting mixture is stirred vigorously for 42 hours at room temperature. The organic layer is separated, and the aqueous layer is extracted with dichloromethane (50 ml). The organic layers are combined and dried. Evaporation of solvent gives a residue which is recrystallized from toluene (150 ml) to give 13.6 g of pure (S)-5-tosyloxymethyl-2-pyrrolidinone, $[\alpha]_D = +7.80 \pm 0.04$ (c=2.64, EtOH).

EXAMPLE 10

(R)-5-Vinyl-2-pyrrolidinone

To a stirred suspension of (R)-4-amino-5-hexenoic acid (2.58 g, 20 mmoles) in methanol (20 ml), thionyl chloride (1.5 ml) is added dropwise with ice cooling. After refluxing for 3.5 hours, evaporation of solvent gives an oil which is dissolved in water (~15 ml). Sodium carbonate (4 g) is added, and the resulting mixture is extracted 3 times with dichloromethane. Drying and evaporation gives the methyl ester as an oil (2.85 g).

NMR(CDCl$_3$): δ1.35 (2H, s(NH$_2$)); 1.62-2.03 (2H, m); 2.17-2.58 (2H, m); 3.32 (1H, q, J=7 Hz); 3.67 (3H, s); 4.87-6.10 (3H, m).

The oil is heated in toluene (bath temperature: 120° C.) for 40 hours. Distillation in a Kugelrohr (0.1 mm Hg, 140° C.) gives the title compound as a colorless oil (1.57 g); $[\alpha]^D$(EtOH, c=4): $-54.84° \pm 0.08°$.

NMR(CDCl$_3$): δ1.47-2.53 (4H, m); 4.13 (1H, broadened q, J=7 Hz); 4.93-6.13 (3H, m); 7.53 (1H, broad s).

EXAMPLE 11

(R)-5-(1',2'-dibromoethyl)-2-pyrrolidinone

To a solution of (R)-5-vinyl-2-pyrrolidinone (1.28 g, 11.5 mmoles) obtained as in Example 10, in carbon tetrachloride (18 ml) is added a solution of bromine (0.67 ml) in carbon tetrachloride (5 ml) dropwise with ice cooling and stirring. During this addition, a viscous oil separates. After the addition, stirring is continued for 1 hour at room temperature. The solvent is removed under vaccuum, and the residue obtained is dissolved in dichloromethane and washed with 10% sodium bisulfite solution until nearly colorless. The aqueous phase is made basic with (solid) sodium carbonate and extracted twice with dichloromethane. The combined organic phases are dried and evaporated to give an oil which is purified by flash chromatography on silica gel (200 g, eluent: hexane/ethyl acetate/chloroform/methanol 3:2:2:1; Rf (same solvent): 0.33). The pure title compound crystallizes on evaporation and is obtained as a white solid 1.54 g).

NMR(CDCl$_3$): δ1.6-2.75 (4H, m); 3.5-3.93 and 3.93-4.53 (4H, 2m); 7.63 (1H, broad s).

EXAMPLE 12

(R)-5-Ethynyl-2-pyrrolidinone

To a suspension of potassium-tert-butoxide (3.57 g) in dry THF (10 ml), cooled at −65° C., a solution of (R)-5-(1',2'-dibromoethyl)-2-pyrrolidinone (1.44 g, 5.31 mmoles) obtained as in Example 11, in THF (20 ml) is added slowly, whereby the internal temperature is kept between −60° C. and −65° C. The mixture is allowed to warm up to −20° C.; then it is poured into a vigorously stirred ice-cold solution of acetic acid (2.5 g) in water (10 ml). The mixture is diluted with ether (50 ml). The aqueous layer is separated, made basic with sodium carbonate, and extracted twice with dichloromethane. The combined organic phases are dried and evaporated to give an oil which still contains acetic acid. It is dissolved in water (~20 ml), and solid sodium carbonate is added until basic. Three extractions with dichloromethane, drying and evaporation give an oil (0.62 g) which is purified by chromatography on silica (100 g; eluent: hexane/ethyl acetate/chloroform/methanol 3:2:2:1; Rf (same solvent): 0.23). Pure title compound is obtained as a white solid (0.33 g): $[\alpha]^D$(EtOH, c=3.1): +15.82°±0.06°.

NMR(CDCl$_3$): δ1.92–2.73 (5H, m); 4.40 (1H, m); 7.95 (1H, broad s).

EXAMPLE 13

(R)-4-Aminohex-5-ynoic acid (R)-5-Ethynyl-2-pyrrolidinone, obtained as in Example 13, is treated with 2N hydrochloric acid at 100° C. for 6 hours. Solvent is removed by evaporation and a crude product is obtained. The crude amino acid product is converted to the methyl ester, N-trifluoroacetyl derivative, and the derivative is analyzed by GC ("chirval"), which indicated an optical purity of 100%, with no S-enantiomer detectable.

What is claimed is:

1. In the pyrolysis of N,N-dimethyl-2-[5′-oxo-2′-pyrrolidine]ethylamine, N-oxide to prepare 5-vinyl-2-pyrrolidinone the improvement wherein an aqueous solution of the pyrolysis distillate is contacted with an acidic ion exchange resin to remove the N,N-dimethyl-2-[5′-oxo-2′-pyrrolidine]ethylamine present as a by product.

2. The improved process of claim 1 wherein the acidic ion exchange resin is a sulfonated, styrene-divinylbenzene copolymer.

3. N,N-Dimethyl-2-[5′-oxo-2′-pyrrolidine]ethylamine or its N-oxide.

4. N,N-dimethyl-2-[5′-oxo-2′-pyrrolidine]ethylamine or its N-oxide in the form of their (S)-enantiomers.

* * * * *